United States Patent [19]

Satoh et al.

[11] Patent Number: 5,291,419
[45] Date of Patent: Mar. 1, 1994

[54] METHOD FOR DIAGNOSING THE LIFE OF A SOLDER CONNECTION

[75] Inventors: Ryohei Satoh; Katsuhiro Arakawa, both of Yokohama; Kiyoshi Kanai, Katsuta; Tsutomu Takahashi, Sakura; Takaji Takenaka; Haruhiko Imada, both of Hadano, all of Japan

[73] Assignees: Hitachi, Ltd., Tokyo; Hitachi Microcomputer Engineering Ltd., Kodaira, both of Japan

[21] Appl. No.: 938,517

[22] Filed: Jan. 6, 1992

Related U.S. Application Data

[63] Continuation of Ser. No. 505,585, Apr. 6, 1990, abandoned.

[30] Foreign Application Priority Data

Apr. 10, 1989 [JP] Japan ............................. 1-87927

[51] Int. Cl.$^5$ .............................................. G01M 5/00
[52] U.S. Cl. .................................. 364/508; 364/578; 364/552; 73/799
[58] Field of Search ................... 364/551.01, 550, 508, 364/552, 578, 505, 506, 507; 73/577, 588, 799

[56] References Cited

U.S. PATENT DOCUMENTS

| | | | |
|---|---|---|---|
| 4,454,585 | 6/1984 | Ele | 364/552 |
| 4,722,062 | 1/1988 | Breitkopf et al. | 364/508 |
| 4,825,284 | 4/1989 | Soga et al. | 357/80 |
| 4,875,170 | 10/1989 | Sakurai et al. | 73/799 |
| 4,947,341 | 8/1990 | Shine | 364/508 |
| 4,975,855 | 12/1990 | Miller et al. | 364/507 |

OTHER PUBLICATIONS

Lin et al., Design Considerations for a Flip-Chip Joining Technique, Solid State Technology, pp. 48-54, Jul. 1970.

"A Thermal Fatigue of Ph-Sn alloy minute connection in electronic circuit", extended abstracts of the 103rd Autumn Convention of NIPPON KINZOKU Gakkai, pp. 144-145, Nov. 1989.

*Primary Examiner*—Thomas G. Black
*Assistant Examiner*—Michael Zanelli
*Attorney, Agent, or Firm*—Antonelli, Terry, Stout & Kraus

[57] ABSTRACT

A method for evaluating the life of a connection between members including the steps of extracting parameters defining the shearing strain of a predetermined model representing the connection thereby to calculate the values of plural shearing strains of the connection, calculating the equivalent strain amplitude corresponding to thermal fatigue stress for each of the values of the plural shearing strains defining the relationship between the shearing strain and the equivalent strain amplitude, formulating a life evaluation criterion equation expressed using the equivalent strain amplitude, calculating, for the connection, the equivalent strain amplitude corresponding to each of the shearing strains actually measured using the equation, and substituting the equivalent strain amplitude for the life evaluation criterion equation to acquire the life of the connection. Further, in this method, an equation for evaluating the advancement of a crack is made using the equivalent strain amplitude, and the equivalent is substituted for the crack advancement evaluation equation to calculate the length of the crack.

18 Claims, 9 Drawing Sheets

Δε ··· ENTIRE STRAIN AMPLITUDE
Δεe ··· ELASTIC STRAIN AMPLITUDE
Δεp ··· PLASTIC STRAIN AMPLITUDE
Δσ ··· STRESS AMPLITUDE

DB...DIAMETER OF CONNECTION,
a... LENGTH OF CRACK,
da/dN...SPEED OF CRACK ADVANCEMENT, $$N = \frac{1}{A} \log \left| \frac{Aa + B}{Aa_0 + B} \right|$$

N...NUMBER OF CYCLES,
$a_0$... LIFE LENGTH OF CRACK,
$a_f$... LIFE NUMBER OF CYCLES,
$N_f$... LIFE NUMBER OF CYCLE,
A, B... CONSTANT,

FIG. 6B
FIG. 6C
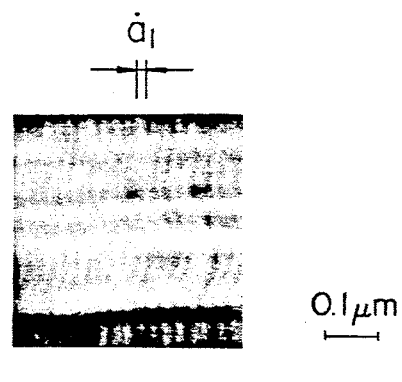
SEM IMAGE AT $\dot{a}_1$
0.1 μm
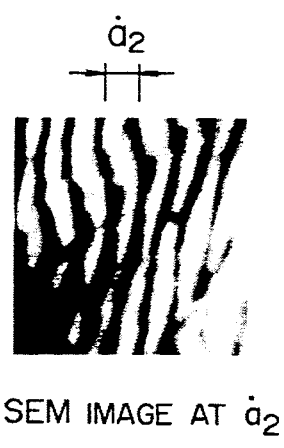
SEM IMAGE AT $\dot{a}_2$

METHOD FOR DIAGNOSING THE LIFE OF A SOLDER CONNECTION

This application is a continuation of U.S. patent application Ser. No. 505,585, filed on Apr. 6, 1990 now abandoned.

BACKGROUND OF THE INVENTION

The present invention relates to a method for evaluating the life of a connection, and more particularly to a method for evaluating the life of a connection which greatly depends on thermal fatigue, such as a solder connection of an electronic circuit device.

With respect to general fatigue life of metal, several methods for evaluating it and life rules therefor, as shown in Table 1, have been proposed on the basis of research and experience of fatigue breakdown accidents. Some of the methods have been put into practice.

Particularly, it is known that the Manson-Coffin rule shown as No. 1 in the table can be used to evaluate the low cycle fatigue life of many metals. The actual life can be evaluated by the Repetition Amendment Speed Equation No. 9 in the table which is obtained by modifying this rule regarding the repetitive frequency f of fatigue and the length a of a crack.

Further, a method for evaluating the life of the solder connection of an electronic circuit device is disclosed in Solid State Technology July (1970) pp. 48–54.

TABLE 1

| No. | DEVELOPER | LIFE EQUATION OR CRACK ADVANCING SPEED EQUATION |
|-----|-----------|-------------------------------------------------|
| 1 | S. S. Manson, L. F. Coffin (Manson-Coffin RULE) | $\Delta\epsilon_p \cdot N^n = C$ |
| 2 | S. S. Manson, G. R. Halford (STRAIN REGION DIVISION TECHNIQUE) | $\Sigma\Phi_f = 1$<br>$\Phi_f = 1/N_{pp} + 1/N_{cc} + 1/N_{cp} + 1/N_{pc}$<br>$\Delta\epsilon_{pp}/D_p = 0.75\, N_{pp}^{-0.6}$<br>$\Delta\epsilon_{pp}/D_p = 0.75\, N_{pp}^{-0.8}$<br>$\Delta\epsilon_{pp}/D_p = 1.25\, N_{pp}^{-0.8}$<br>$\Delta\epsilon_{pp}/D_p = 0.25\, N_{pp}^{-0.8}$ |
| 3 | H. W. Liu | $d_a/d_N = C(\Delta\sigma)^2 a$<br>$\Delta\sigma = \sigma_{max} - \sigma_{min}$ |
| 4 | P. C. Paris (Paris RULE) | $d_a/d_N = C(\Delta K)^n$<br>$\Delta K = K_{man} - K_{min}$ |
| 5 | G. Welter, J. A. Choquet | $d_a/d_N = (C\epsilon_{TR}\sqrt{a})$<br>$\epsilon_{TR} = \epsilon_p + \epsilon_e$ |
| 6 | T. Yokobori (KINETICS MODEL OF DISLOCATION) | $d_a/d_N = Cf^m \Delta K^n \exp(-Q/kT)$ |
| 7 | W. Elber (RULE OF COEFFICIENT ENLARGING EFFECTIVE STRESS) | $d_a/d_N = C(\Delta K_{eff})^n$<br>$\Delta K_{eff} = K_{max} - K_{op}$ |
| 8 | J. R. Rice, P. C. Paris | $d_a/d_N = C(\Delta J)^n$ |
| 9 | H. D. Solomon, L. F. Coffin (REPETITION AMENDMENT SPEED RULE) | $d_a/d_N = Ca(\Delta\epsilon_p)^{n/m}$ |
| 10 | K. Tanaka, S. Taira | $d_a/d_N = C(\Delta\Phi)^n$ |

(N; LIFE), $\Delta\epsilon p$; PLASTIC STRAIN AMPLITUDE), (C, n, m; CONSTANT), ($N_{pp}$, p p WAVEFORM LIFE), ($N_{cc}$; c c WAVEFORM LIFE), ($N_{cp}$; c p WAVEFORM LIFE), ($N_{pc}$; p c WAVEFORM LIFE), ($D_p$; PULLING FRACTURE DUCTILITY AT A HIGH TEMPERATURE FOR SHORT TIME), (Dc; CREEP FRACTURE DUCTILITY), $\Delta\sigma$; STRESS RANGE), ($\Delta K$; RANGE OF COEFFICIENT ENLARGING STRESS), (a; CRACK LENGTH), ($\Delta\epsilon_{TR}$; ENTIRE STRAIN RANGE), ($\Delta\epsilon_p$; PLASTIC AND ELASTIC STRAIN RANGE), (f; REPETITION FREQUENCY), (Q; ACTIVATION ENERGY), (k; BOLTAMANN's CONSTANT), (T; TEMPERATURE), ($\Delta K_{eff}$; RANGE OF COEFFICIENT ENLARGING EFFECTIVE STRESS), ($K_{op}$; K AT CRACK OPENING), ($\Delta J$; INTEGRATION RANGE), ($\Delta\Phi$; RANGE OF DISPLACEMENT OF CRACK OPENING)

To account for the influence of distortion amplitude on fatigue life, generally, the plastic distortion amplitude $\Delta\epsilon_p$ in the life equations of Nos. 1 and 9 in Table 1 is adopted. $\Delta\epsilon_p$ is defined as the range of distortion in the hysterisis stress-strain curve when mechanical stress is repeatedly applied to a material.

However, this $\Delta\epsilon_p$ at a solder connection cannot be measured by the conventional techniques shown listed in Table 1. The reason therefor is as follows. If a temperature as high as the melting point of solder changes at e.g. a solder connection of a flip chip for an electronic circuit device, because of a difference between the flip chip and a substrate in their thermal expansion coefficient, the stress-strain occurring in the solder becomes a three-dimensional stress-strain state, and further changes because of the great dependency of the solder itself on temperature. In this way, the above conventional methods do not pay attention to the influences from a temperature cycle in estimating the range of distortion. For example, the junction between the flip chip for an electronic circuit and a substrate is subjected to great temperature change; its temperature will increase up to immediately below the melting point of solder (183–320° C. in Pb-Sn series) because of heat generation in electronic components and environmental temperature. Nevertheless, the conventional techniques do not take such a temperature change in to account so that they cannot correctly evaluate the life of the junction subjected to the thermal fatigue. More specifically, the advancing speed of a crack at the connection depends on the shape of the connection. The above conventional techniques do not take this consideration;

therefore, they cannot know the remaining sectional area so that they cannot design the weight resistance and current capacity of the connection. Particularly, the technique disclosed in the above reference Solid State Technology takes only shearing strain $\gamma_{max}$ into consideration but does not take temperature dependency of the stress-strain of the solder for this shearing strain. Therefore, this technique also cannot evaluate the life of the junction or connection subjected to thermal fatigue. Thus, the conventional life evaluation methods cannot correctly evaluate the life of the connection causing many poor quality products to be made.

SUMMARY OF THE INVENTION

An object of the invention is to provide a method for evaluating the life of a connection with high accuracy for a short time through a relatively simplified process.

This object can be attained by adopting $\Delta\epsilon_{eqmax}$ with higher precision as a strain amplitude which is an index of the thermal fatigue and taking into consideration the temperature dependency and a crack advancing speed in connection with an estimation of $\Delta\epsilon_{eqmax}$.

The $\Delta\epsilon_{eqmax}$, which is a maximum equivalent strain of the connection, can be an optimum index of the thermal fatigue which is disclosed in the extended abstracts of The 103rd Autumn Convention of Nippon Kinzoku Gakkai, pp. 144-145, Nov. 1989.

Prior to explaining the concept of the maximum equivalent strain, an equivalent stress-equivalent strain will be defined. The equivalent strain is generally defined from the field condition in a three-axis-strain field in material mechanics, i.e. Mises condition. The corresponding stress is the equivalent stress. Since a true single-axis pulling stress-true strain curve concerning polycrystalline soldering material can be regarded as taking uniform deformation of the soldering material, which is an ordinally solder connecting portion itself, the curve itself is considered as equivalent pulling stress-equivalent strain curve.

The equivalent strain amplitude can be defined as follows. When the connection is subjected to the temperature cycle as shown in FIG. 3, the stress-strain curve occurring in the solder at the connection changes in accordance with the temperature change ① to ⑦ in this temperature cycle. This change in the stress-strain curve is shown as ① to ⑦ in FIG. 2 which can be acquired by the finite-element method three-dimensional thermal elastic/plastic analysis taking into consideration the temperature dependency of the real stress-real strain of the solder. Specifically, when in FIG. 3, temperature rises from the initial state ① to 50° C. (②), the maximum stress-strain of the solder (e.g. ②) stays anywhere in the real stress-real strain curve from ① to 50° C. in FIG. 2. Likewise, one cycle of temperature change of 150° C.→50° C.→20°results in the change in the stress-strain of ③ - ④ - ⑤ - ⑥ - ⑦. Then, assuming that this change corresponds to the stress-strain hysterisis curve shown in FIG. 1, its maximum equivalent amplitude $\Delta\epsilon_{eqmax}$ is defined as the strain range between a high temperature 150° C. to a low temperature $-50°$ C. as shown in FIG. 2. The maximum equivalent amplitude $\Delta\epsilon_{eqmax}$ thus defined and the life $N_f$ can be correlated with high accuracy irrespectively of the shape of the connection and the temperature range, as disclosed in the above mentioned extended abstracts.

Another object of the present invention is to provide a criterion equation for evaluating the life and a criterion equation for evaluating the degree of a crack using the maximum equivalent amplitude $\Delta\epsilon_{eqmax}$ and an equation representative of the speed of crack advancement. This crack advancement speed can be experimentally acquired in temperature cycle test by observing the breaking face of the solder with the crack advanced by an electron microscope.

In order to attain another object of the present invention, an approximation equation for acquiring the maximum equivalent strain amplitude $\Delta\epsilon_{eqmax}$ is simply obtained using the size of electronic components, the characteristic of the solder, and the condition of the temperature cycle. This approximation equation is programmed for a computer.

The crack advancement speed equation permits the life of the connection to its final breakdown to be estimated before the final breakdown.

The life evaluation criterion equation and the crack advancement criterion equation can give the number of temperature cycles for the degree of crack advancement permitted for assuring a remaining sectional area, and so gives the life of the connection. Contrary to this, these equations can also give the degree of crack advancement for the number of necessary cycles to know the remaining sectional area. This a product can be designed so that it will not program to a date of poor quality within its life.

The approximation equation for acquiring the maximum equivalent strain amplitude can give the maximum equivalent strain amplitude by a simple operation for a short time so that the life evaluation criterion equation and the crack advancement criterion equation acquired using the value of the maximum equivalent strain amplitude permits the life and the degree of crack advancement to be calculated, thereby designing an electronic device with high accuracy.

BRIEF DESCRIPTION OF THE DRAWINGS

FIGS. 6B and 6C are SEM images at $a_1$ and $a_2$ on the crack, respectively;

DESCRIPTION OF THE PREFERRED EMBODIMENTS

Figure 4A:
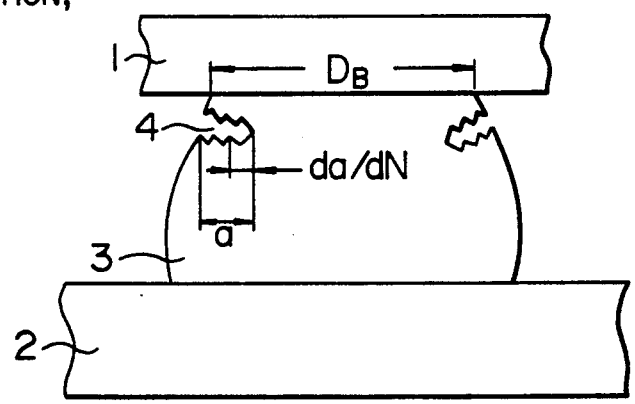
FIG. 4A is a conceptual view of the crack occurring in the solder between a semiconductor integrated circuit and a substrate in an embodiment of the present invention.
Figure 5:
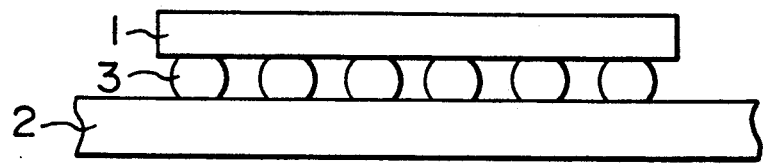
FIG. 5 is a side view of the solder connection between the semiconductor integrated circuit and the substrate which is a basis of the partially enlarged model of FIG. 4A.

An embodiment of the present invention will be explained with reference to the drawings. FIG. 5 shows the state where a semiconductor integrated circuit 1 is connected with a circuit substrate 2 through solders. If the temperature cycle of temperature changes due to repeated power on/off of the circuit then, because of a difference between the semiconductor integrated circuit 1 and the circuit substrate 2 in their thermal expansion coefficient, strains occur repeatedly in the solder connections 3 eventually causing the solder to crack as shown in the partially enlarged view of FIG. 4A. For each of the temperature cycles, this crack will advance by an interval $d_a/d_N$ and also a notch remains on the breaking face on which the crack occurs. The interval $d_a/d_N$ is referred to as a crack advancement speed ($D_B$: diameter of connection).

Figure 6A:
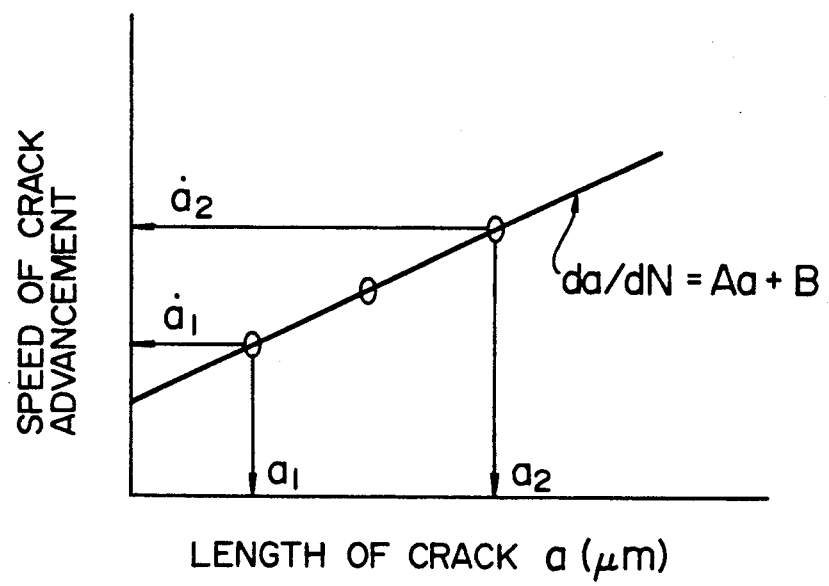
FIG. 6A is a graph showing a crack advancement speed equation $da/dN = Aa + B$ which is defined by the relationship between the length a of a crack and a crack advancement speed.
Figure 6D:
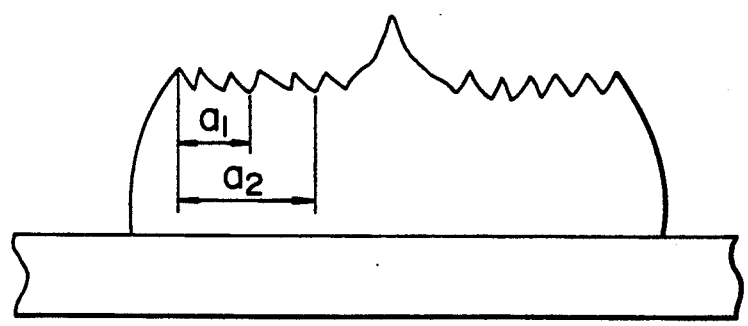
FIG. 6D is a side view of the solder section where the semiconductor integrated circuit is mechanically removed from when the crack advances to point a2.

After the electronic device shown in FIG. 5 has been subjected to 1000 (one thousand) cycles of temperature change, the semiconductor integrated circuit 1 is mechanically removed therefrom. The faces of the crack 4 thus formed, as shown in FIG. 6D, are observed using a scanning type electronic microscope (SEM). FIGS. 6B and 6C show the observed images. The crack advancement speeds $d_a/d_N$ at the ends of the lengths of $a_1$ and $a_2$, which are obtained from the observed images of FIGS. 6B and 6C, are $å_1$ and $å_2$. As a result of these observation results and other observations, as seen from FIG. 6A, the relationship between the crack advancement speed and the crack length a can be approximated as a linear relationship $$d_a/d_N = A_a + B \qquad (1)$$

Figure 4B:
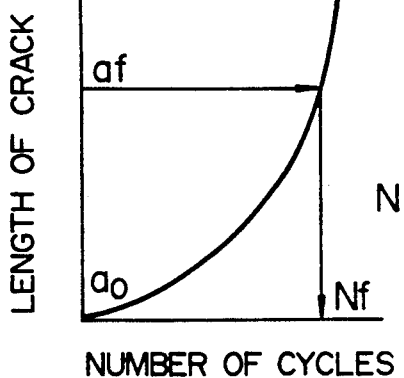
FIG. 4B is a graph showing the relation between the length a of a crack and the number N of cycles giving rise to the life on the basis of the model of FIG. 4A.

By integrating this equation (1), as shown in FIG. 4B, an equation for evaluating the life of a connection, i.e.

$$N = \frac{1}{A} \log \left| \frac{A_a + B}{A_{ao} + B} \right| \qquad (2)$$

(A, B: constant, a: length of crack, $a_o$: initial length of crack, N: number of cycle) and a graph for evaluating the life can be obtained. Thus, the number of temperature cycles indicative Of the life can be acquired from the crack length $a_f$ which is a criterion for the life (Generally it is assumed that when the crack advances to the center of the connection solder, the life ends, i.e. $D_B/2 = a_f$ ($D_B$: diameter of the connection solder)).

The life to breakdown estimated for the number of testing temperature cycles of 1000 is set for 3000 cycles. As a result of continued testing under the same condition, the breakdown was electrically confirmed at 3300 cycles approximate to the estimated 3000 cycles.

Figure 1:
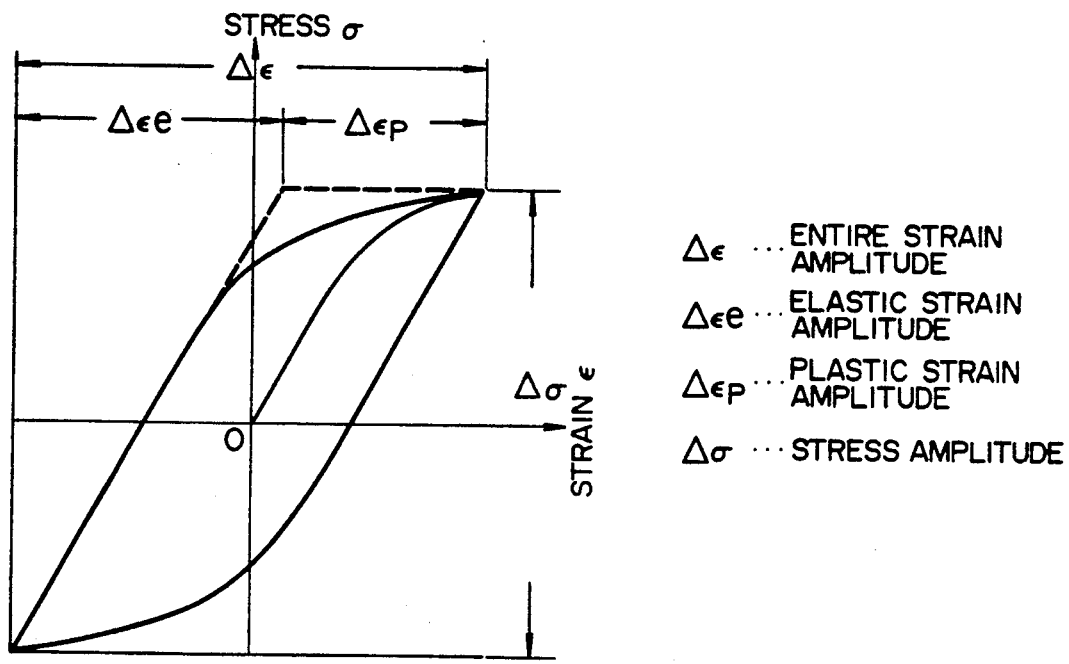
FIG. 1 is a view of the conventional stress-strain hysterisis curve due to fatigue.
Figure 2:
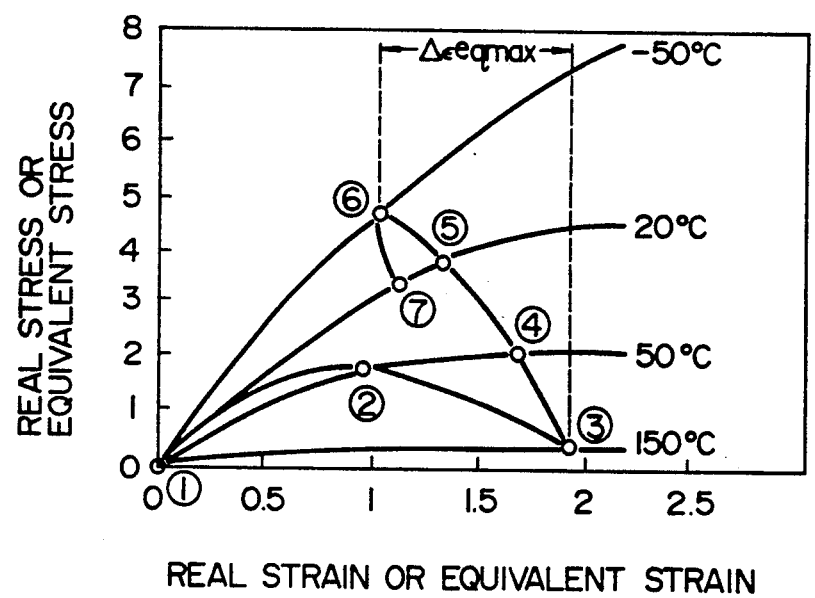
FIG. 2 is a graph of the equivalent stress-strain curve of thermal fatigue which is adopted in an embodiment of the present invention.
Figure 3:
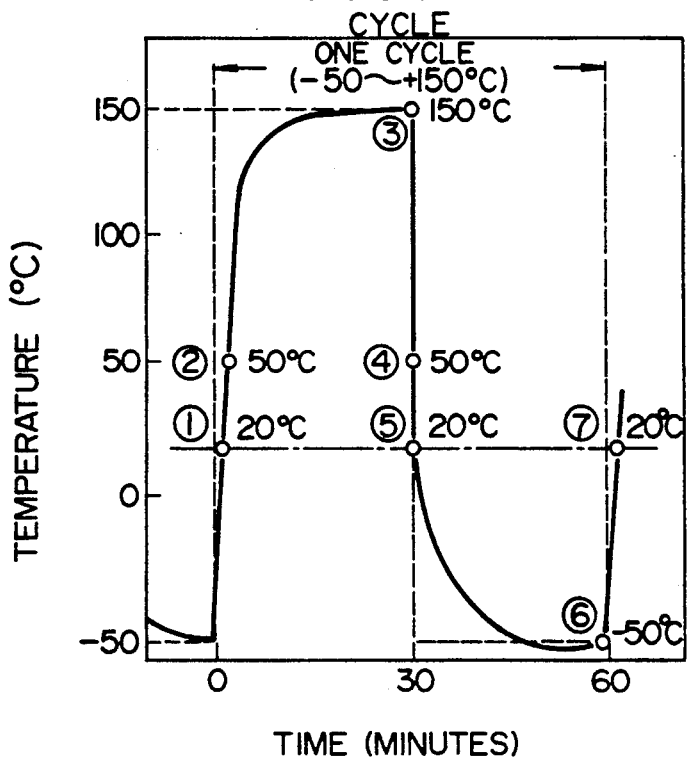
FIG. 3 is a graph showing the temperature profile used in an embodiment of the present invention.
Figure 7:
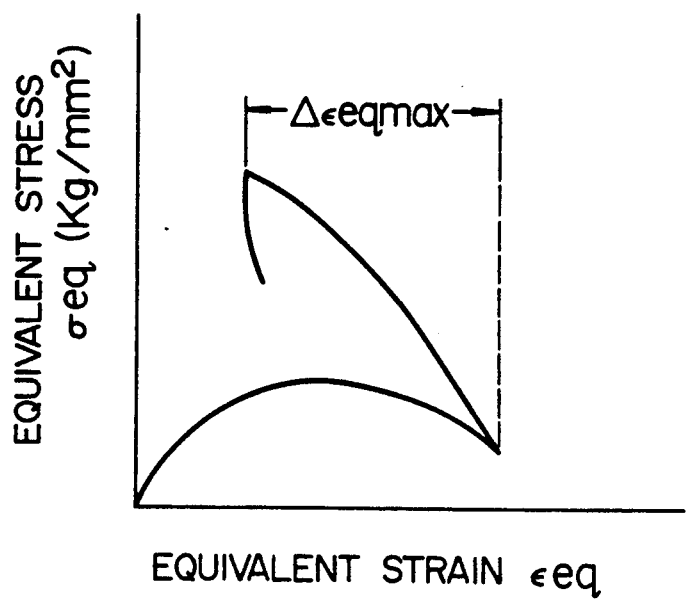
FIG. 7 is a graph of an equivalent stress-strain curve at a point in a solder connection which is acquired by the method of FIG. 2 through the finite element method three-dimensional thermal elastic/plastic analysis.

Further, the solder connection structure shown in FIG. 5 is subjected to the temperature change corresponding to the testing temperature cycle of room temperature →+150° C.→−50° C.→room temperature through the finite element method three-dimensional thermal elastic/plastic analysis as shown in FIG. 2. Then, the crack 4 as shown in FIG. 4A occurs in the solder connection structure. The hysterisis curve of the equivalent stress-equivalent strain at the crack 4 is shown in FIG. 7. As seen from FIG. 7, the strain amplitude is defined as the maximum equivalent strain amplitude $\Delta\epsilon_{eqmax}$. The relationship between the maximum equivalent amplitude $\Delta\epsilon_{eqmax}$, and the crack advancing speed $d_a/d_N$ and the crack length a acquired in the previous breakdown test can be expressed by $$d_a/d_N = C(A_a + B) \cdot (\Delta\epsilon_{eqmax}) \qquad (3)$$

Equation (3) physically represents that the crack advancing speed $d_a/d_N$ increases with the increase of the strain amplitude $\Delta\epsilon_{eqmax}$, and the life increases with the increase of the length of the connection for the same strain amplitude $\Delta\epsilon_{eqmax}$.

By integrating Equation (3), the life $N_f$ can be acquired by the life evaluating criterion equation expressed by the following.

By using $N_f$ for expressing life number of cycles which causes fracture, $a_o$ for an initial defect, $a_f$ for a crack length when fractured, the above mentioned life evaluating criterion equation is expressed by, $$\int_0^{N_f} dN = \frac{1}{C} \cdot (\Delta\epsilon_{eqmax})^{-n} \int_{a_o}^{a_f} \frac{1}{A_a + B} da \qquad (4)\text{-}1$$

$$N_f = \frac{1}{C} \cdot (\Delta\epsilon_{eqmax})^{-n} \log \frac{|A_{af} + B|}{|A_{ao} + B|} \qquad (4)\text{-}2$$

where, n is a material constant and c is a constant. ($a_f$: life length of crack)

Figure 8:
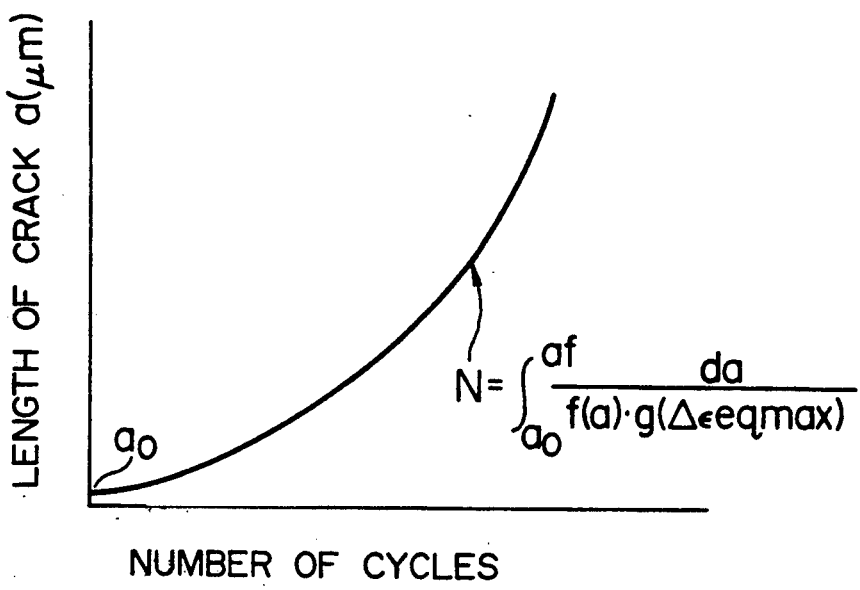
FIG. 8 is a graph showing the criterion for evaluating the life which is defined by the relationship between the crack length a and the cycle number N taking the equivalent strain into consideration.

Further, by calculating backwards from Equation (4)-2, the crack length a after N cycles can be acquired by the crack advancement evaluating equation expressed by equation (5). These relations are exemplified in FIG. 8.

$$a = \frac{1}{A} \{(A_{ao} + B)\exp\{C \cdot N(\Delta\epsilon_{eqmax})^n\} - B\} \qquad (5)$$

With respect to poor quality products, the actual life thereof is 3500 cycles which is very approximate to the life of 3200 cycles acquired from calculation, where values of $\Delta\epsilon_{eqmax} = 0.01$ (=1%), A: $8.18 \times 10^{-3}$, B: 0.18, C: 0.23, Af: 100 μm and $a_o$: 0 are employed.

Meanwhile, the maximum equivalent strain amplitude $\Delta\epsilon_{eqmax}$, which is decisive for the life of the solder connection due to thermal fatigue, greatly depends on the size of the semiconductor integrated circuit and the environmental condition for the same connection structure; to acquire it through the infinite element method three-dimensional elastic/plastic analysis is very troublesome. Then, with reference to FIG. 10, a technique for simply acquiring the maximum equivalent strain amplitude $\Delta\epsilon_{eqmax}$ will be explained.

Figure 9:
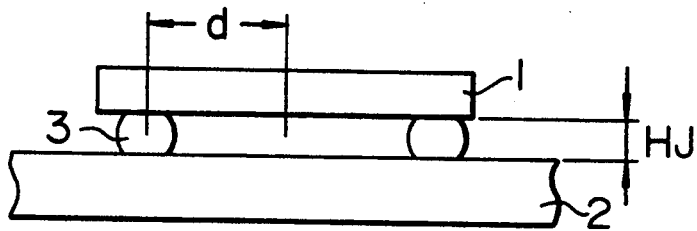
FIG. 9 is a side view showing the main size of each of the substrate, the solder and the electronic circuit component.
Figure 10:
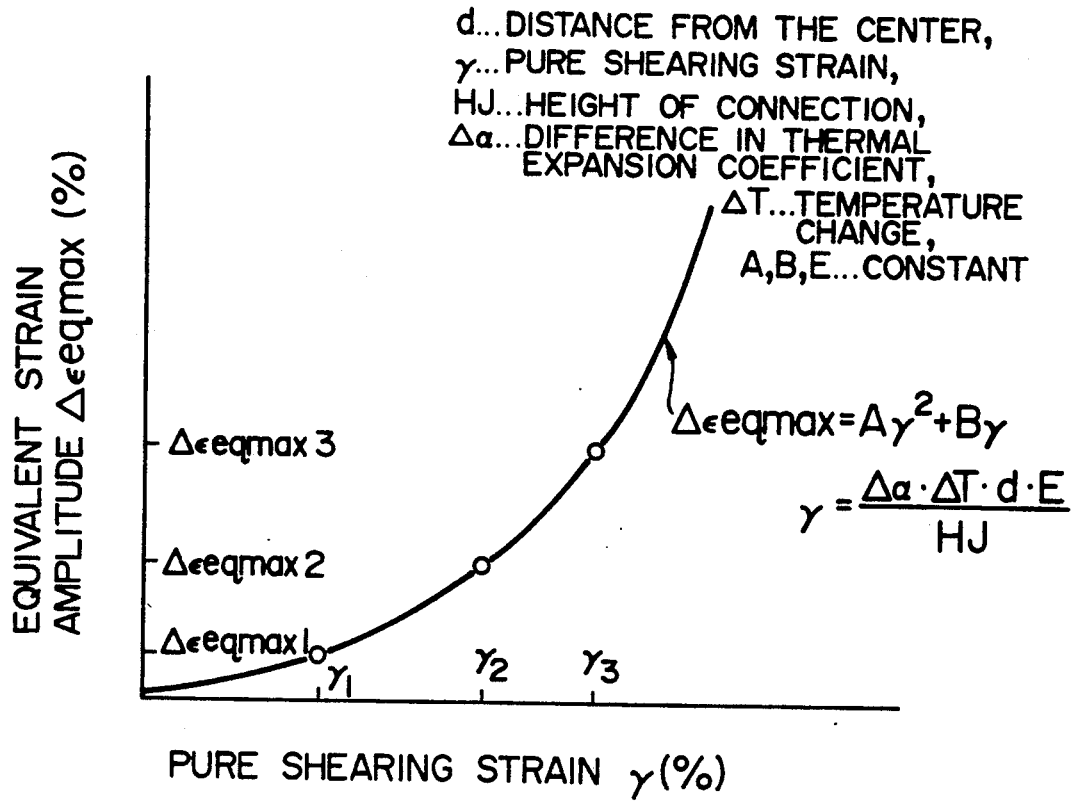
FIG. 10 is a graph showing the strain evaluation criterion for acquiring the equivalent strain amplitude from a pure shearing strain.
Figure 12:
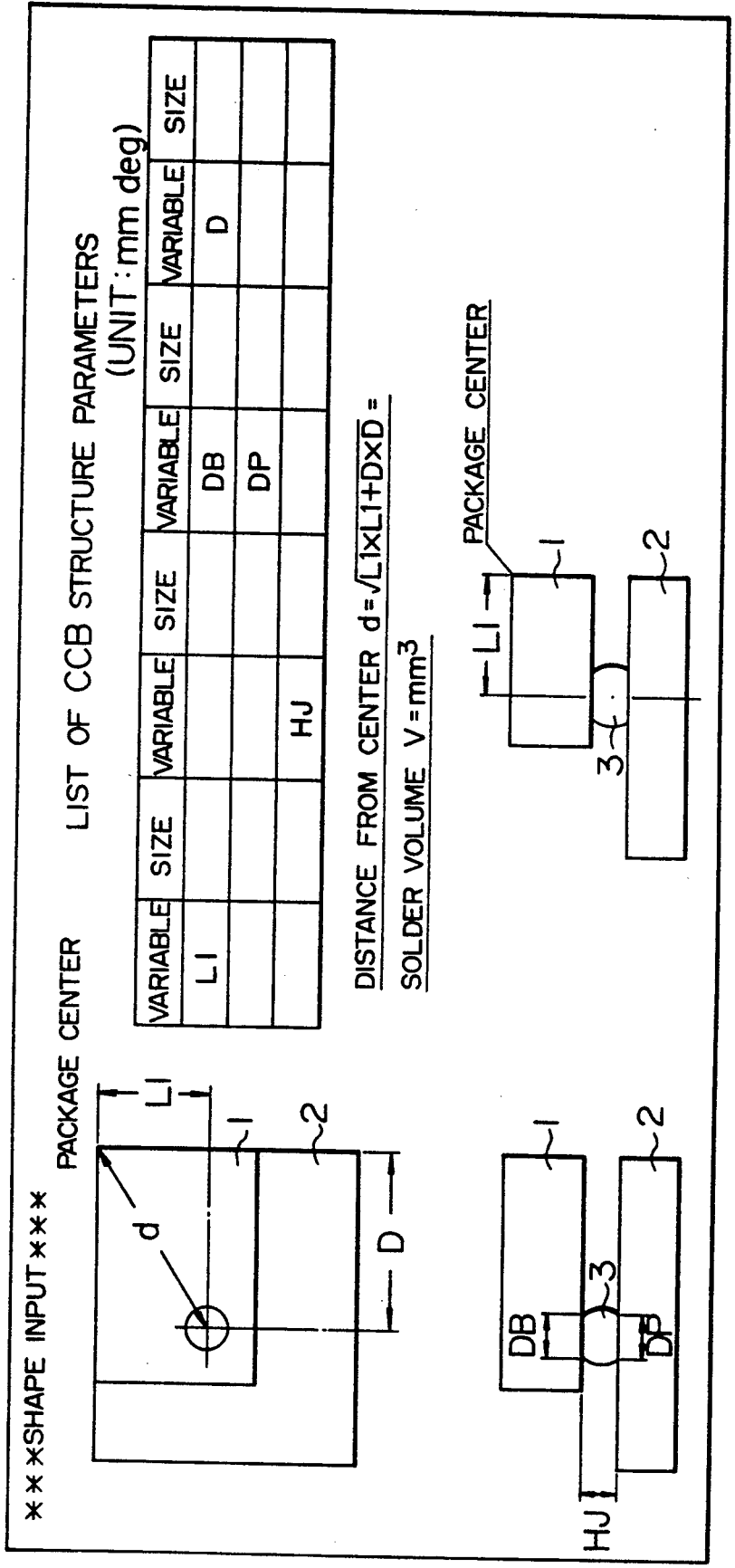
FIGS. 12 and 13 are views showing examples of display on a display device which are outputted as a result of the program processing of FIG. 11.
Figure 13:
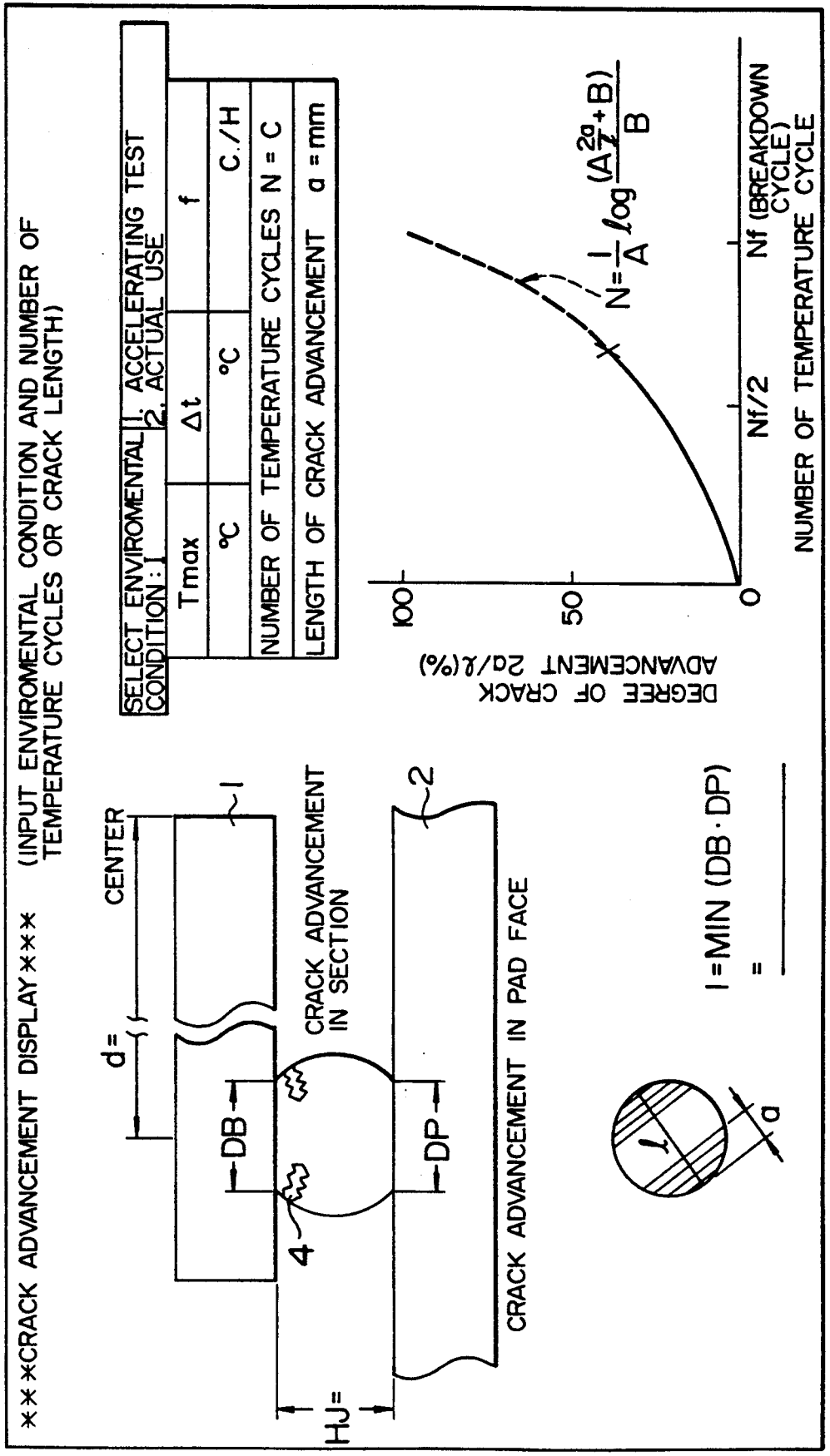

Generally, the shearing strain $\gamma$ at the connection as shown in FIG. 9 can be expressed by $$\gamma = \frac{\Delta\alpha \cdot \Delta T \cdot d \cdot E}{HJ} \qquad (6)$$

where d is the size of the semiconductor integrated circuit, HJ is the height of the connection, $\Delta\alpha$ is the difference between the semiconductor integrated circuit 1 and the circuit substrate 2 in their thermal expansion coefficient $\Delta T$ is the temperature difference therebetween in their temperature cycles, and E is a correction parameter depending on the shape of the connection. The maximum equivalent strain amplitudes $\Delta\epsilon_{eqmax}1$, $\Delta\epsilon_{eqmax}2$ and $\Delta\epsilon_{eqmax}3$ corresponding to concrete values $\gamma_1$, $\gamma_2$, and $\gamma_3$ can be simply acquired. The values $\gamma_1$, $\gamma_2$, and $\gamma_3$ are obtained by a manual calculation of a structure model as shown in FIGS. 12 and 13 in which certain dimensions are assigned, and $\Delta\epsilon_{eqmax}1,2,3$, are obtained by finite element three-dimensional thermal elastic/plastic analysis. By connecting these points, an approximation curve as shown in FIG. 10 can be made so that an approximation equation for acquiring $\Delta\epsilon_{eqmax}$ from $\gamma$ can be provided. It is discovered that the equation can be expressed using $\gamma$ by $$\Delta\epsilon_{eqmax} = A'\gamma^2 + B'\gamma \qquad (7)$$

This equation permits the maximum equivalent strain amplitude to be simply calculated. Further, the life $N_f$ and the crack advancing degree a can also be simply acquired from Equations (4) and (5), respectively. Additionally, if there is a temperature difference between the electronic component, i.e. the semiconductor integrated circuit, and the circuit substrate, the shearing strain $\gamma$ can be more generally expressed by $$\gamma = \frac{(\alpha_1 \cdot T_1 - \alpha_2 \cdot T_2) d \cdot E}{HJ} \qquad (8)$$

where $\alpha_1$ and $T_1$ are the thermal expansion coefficient and temperature of the semiconductor integrated circuit $\alpha_2$ and $T_2$ are those of the circuit substrate.

In accordance with this embodiment, the life of the solder connection can be evaluated or estimated simply and correctly.

Figure 11:
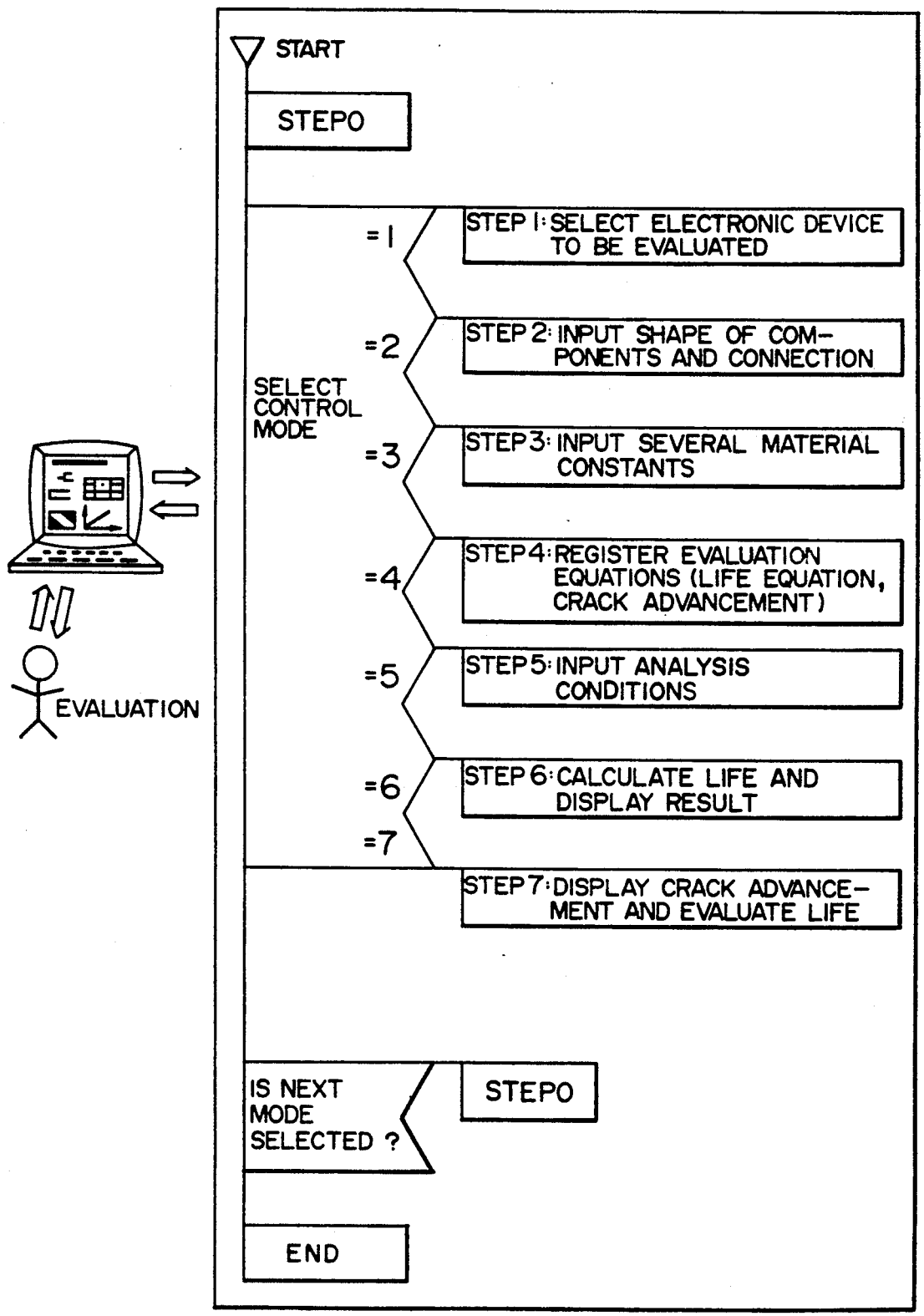
FIG. 11 is a flow chart of the program for performing an evaluation processing using the method according to the present invention.

Now an explaination will be given for another embodiment of the present invention which realizes the life evaluation method according to the present invention through a program. The flowchart of the entire program is shown in FIG. 11. The screen image displayed when the shape of the solder connection of the electronic component (flip chip or CCB chip) is input, and that displayed when the result of life evaluation and the degree of crack advancement are output are shown in FIGS. 12 and 13.

The evaluation through the program is carried out in the following process.

In Step 1, an object electronic component is designated by a key operation; for example, CCB is selected from a group consisting of CCB (Controlled Collapse Bonding), QFP (Quad Flat Package), PLCC (Plastic Leaded Chip Carrier), MSP (Mini Square Package), and flip chip etc. The selection operation in Step 1 displays the model of the CCB chip described by trigonometry as shown in FIG. 12. With respect to the substrate 2, the CCB package chip 1 and the solder 3 connecting them, the items indicated as the shape data to be input for the CCB model are the distance d from the package center to the solder; the width direction distance D and longitudinal direction distance $L_1$ from the package center to the solder; the connecting width DB of the solder 3 on the side of the package 1; that DP thereof on the side of the substrate 2; and the height HJ of the package from the substrate 2.

In Step 2, the items or parameters required are input in such a manner that the respective columns of the list displayed for the CCB are filled with the corresponding data by a key operation. By filling the list with the required items in accordance with the items of the package model displayed by trigonometry, they can be surely input.

In Step 3, thermal expansion coefficients of the substrate 2 and the package (CCB) are input. By this step, parameters, except for $\Delta T$, required for calculation in equation (6) are input.

In Step 4, Equation (4), which is a criterion equation for evaluating the life of the solder connection, and Equation (5), which is an equation for evaluating the crack advancement, are input, and further constants and an index n are input. These equations can be read out from the sub-routine including model equations prepared for each of the substrates and packages, and thereafter the constants and the index are substituted for the equations.

In Step 5, analysis conditions such as the upper and lower limit temperatures in the temperature cycle, the repetition frequency thereof, and the temperature difference between the substrate and package are input. Then, in Step 6, if the program is operated, $\gamma$ in equation (6) and $\Delta\epsilon_{eqmax}$ in equation (7) are sequentially calculated according to input parameters and analysis conditions. The obtained values in equations (6) and (7) are used to calculate life time in calculation of life time equation (4)-1 and crack advancement equation (5).

Finally, in Step 7, the crack advancement on a section of the CCB model and on the solder pad surface as shown in FIG. 13 is displayed. The crack advancement display as shown in FIG. 13 also includes the display of the maximum temperature, the temperature difference between the substrate and package, the repetition frequency, the present number of temperature cycles and the present length of crack advancement. From these displays, the degree of crack advancement in the solder connection and the remaining life thereof can be easily evaluated.

Additionally, the above life evaluation process can be repeated from any step thereof, and can also be applied to a flat package IC and the other chip components.

In accordance with the present invention, several calculations in the above program can be easily carried out using a large scale computer or a personal computer thereby permitting the design of the life of the electronic devices.

The life number of temperature cycles and the life degree of crack advancement estimated for a sample prepared for life test in accordance with the present invention agree with those actually measured within an error range of ±10%. Also, the time required for estimation is as short as 5–10 minutes. this time is much shorter than 2–5 hours (measured in the CPU time) required to calculate the maximum equivalent strain amplitude through the infinite element method using a super computer S810 in the previous embodiment. In short, in accordance with the present invention, the process for evaluating the life of the solder connection of an electronic component, which has been difficult, can be carried out in a short time and at low cost using a personal computer or a large scale computer.

Further, the life of the connection can be evaluated through the infinite element method three-dimensional thermal elastic/plastic analysis for any temperature distribution and environmental condition; it can be evaluated with high accuracy. Thus, the life evaluation method according to the present invention can contribute to enhance the reliability of electronic devices which will be strictly demanded in the future.

We claim:

1. A method for diagnosing a connection life of a solder connection between a substrate and parts loaded thereon, said method being performed by a computer, said computer having input means for inputting information and processing means for processing said input information and outputting a result of said processing, said method comprising the steps of:

preparing a plurality of solder connections of the same connection structure with different connection parameters;

determining by said processing means shearing strains and equivalent strain amplitudes of each of said solder connections to determine an approximated shearing strain/equivalent strain amplitude correlation model pertinent to a corresponding one of said solder connections;

applying a number of heat cycles to said solder connections to cause cracks in each of said solder connections;

measuring a total crack length after said heat cycles and a particular crack advancement caused by the very last cycle of said heat cycles to obtain a crack length/crack advancement speed correlation model;

determining a solder connection life diagnosing model with said equivalent strain amplitude by integrating said crack length/crack advancement speed correlation model;

measuring a shearing strain of a solder connection to be diagnosed of said same connection structure with a desired parameter to obtain a corresponding equivalent strain amplitude by using said approximated shearing strain/equivalent strain amplitude correlation model; and determining a connection life of said solder connection with said desired parameter by applying said equivalent strain amplitude of said solder connection with said desired parameter into said connection life diagnosing model.

2. A method for diagnosing a connection life of a solder connection according to claim 1, wherein said relationship between said values of said plural shearing strains and said values of said equivalent strain amplitudes is represented by $$\Delta \epsilon_{eqmax} = A\tau^2 + B'\tau, \tau = \frac{\Delta \alpha \cdot T \cdot d \cdot E}{HJ}$$

where $\Delta \epsilon_{eqmax}$ is the maximum equivalent strain of the connection, $\gamma$ is a pure shearing strain, A is a constant, d is the distance from a center, $\Delta \alpha$ is the difference in a thermal coefficient, E is a constant, HJ is the height of the solder connection, and T is a temperature change.

3. A method for diagnosing a connection life of a solder connection according to claim 1, wherein said connection life diagnosing model is represented by the equation:

$$N_f = \frac{1}{C} \log \frac{|A_{af} + B|}{|A_{ao} + B|} (\Delta \epsilon_{eqmax})^{-n}$$

where $N_f$ is the life number of temperature cycles which causes a fracture; A, B, and C are constants; af is the life length of a crack; ao is the initial length of the crack; and $\Delta \epsilon_{eqmax}$ is the maximum equivalent strain of the connection.

4. A method for diagnosing a connection life of a solder connection according to claim 1, wherein a model for diagnosing the advancement of a crack is made using said equivalent strain amplitudes, and said equivalent strain amplitude is substituted into said model for diagnosing crack advancement to diagnose the length of the crack.

5. A method for diagnosing a connection life for a solder connection according to claim 4, wherein said model for diagnosing crack advancement is represented by $$a = \frac{1}{A} \{(A_{ao} + B)\exp\{C \cdot N(\Delta\epsilon_{eqmax})^n\} - B\}$$

where $\Delta\epsilon_{eqmax}$ is the maximum equivalent strain of the connection; a is the length of a crack; N is the number of cycles; A, B, C are constants; and ao is the initial length of the crack.

6. A method for diagnosing a connection life of a solder connection according to claim 5, wherein said parts loaded on said substrate comprise chip parts connected with said substrate through said solder connection.

7. A method for diagnosing a connection life for solder connection according to claim 6, wherein said chip parts are any one selected from the group consisting of CCB, QFP, PLCC, MSP, flip chip, condenser and resistor.

8. A method for diagnosing a connection life of a solder connection according to claim 5, wherein said shearing strain $\tau$ is defined as $$\tau = \frac{\Delta\alpha}{HJ} \cdot \Delta T \cdot d \cdot E$$

where $\Delta\alpha$ is the difference between the members in their thermal expansion coefficient, $\Delta T$ is a temperature change, d is the size of the electronic device, E is a correction parameter, and HJ is the height of the connection.

9. A method for diagnosing a connection life of a solder connection according to claim 1, wherein said life of the connection is defined as the number of heat cycles at which the connection is broken.

10. A method for diagnosing a connection life of solder connection according to claim 1, wherein said values of said equivalent strain amplitudes are acquired from the relationship between said values of said equivalent strain amplitudes, which are prepared by a finite element method three-dimensional thermal elastic/plastic analysis, and said values of said shearing strains.

11. A method for diagnosing a connection life of a solder connection according to claim 1, wherein said parts loaded on said substrate comprise an electronic device, and said shearing strain occurs in said solder connection.

12. A method performed in a computer, for diagnosing a connection life of a solder connection between a substrate and parts loaded thereon, said computer including input means for inputting information, processing means for processing said input information and outputting a result of said processing and display means for displaying said results of said processing, said method comprising the steps, performed by said computer, of:

inputting by said input means parameters of a plurality of different solder connections of the same connection structure;

calculating by said processing means shearing strains of said plurality of different solder connections;

calculating by said processing means equivalent strain amplitude corresponding to thermal fatigue lifetime for each of the values of said plurality of shearing strains;

defining by said processing means a relationship between said shearing strains and said equivalent strain amplitudes;

formulating by said processing means a life evaluation criterion equation expressed using said equivalent strain amplitude;

inputting by said input means a total crack length and a particular crack advancement by the very last cycle of a number of heat cycles applied to said plurality of different solder connections;

determining by said processing means a crack length/crack advancement speed correlation model thereby obtaining solder connection life diagnosing model with said equivalent strain amplitude;

inputting a desired parameter of said solder connection to be diagnosed of said same connection structure;

determining by said processing means a corresponding equivalent strain amplitude corresponding to said desired parameter by using a relationship between said shearing strain and said equivalent strain amplitudes, substituting said equivalent strain amplitudes for the life evaluation criterion equation to acquire the connection life of said desired parameter; and displaying by said display means the life of said connection;

wherein an equation for diagnosing the advancement of a crack is made using said equivalent strain amplitudes, and said equivalent strain amplitude is substituted for a crack advancement diagnosing equation to calculate the length of the crack;

wherein said inputting step includes the steps of defining a member for which the life of the solder connection is to be diagnosed to display on said display means a shape model of the member, inputting by said input means required parameters representative of the shape of the connection in accordance with the shape model displayed on said display means, inputting required material constants for the member to be evaluated, and inputting an analysis condition of the member to be evaluated;

said method further includes the step, performed by a computer, of performing by said processing means a calculation in accordance with said solder connection life diagnosing model and said crack advancement diagnosing equation; and wherein said displaying step includes the step of displaying the calculation result as a length of the crack on the shape model on the display means, and illustrating said diagnosing result on a solder connection life diagnosing graph representative of the relationship between the number of temperature cycles and the length of the crack.

13. A method for diagnosing a connection life of a solder connection according to claim 12, wherein said solder connection life diagnosing model and said crack advancement diagnosing equation are stored in a memory of said computer as a sub-routine after being once obtained.

14. A method for diagnosing a connection life of a solder connection according to claim 12, wherein said step of defining the member is performed by selecting a chip part; and wherein said chip part is selected from any one of a group consisting of CCB (Controlled Collapse Bonding, QFP (Quad Flat Package), PLCC (Plastic Leaded Chip Carrier), MSP (Mini Square Package), flip chip, condenser and resistor.

15. A method for diagnosing a connection life of a solder connection according to claim 12, wherein said shape model shows the connection relationship between the members by trigonometry.

16. A method for diagnosing a connection life of a solder connection according to claim 12, wherein said parameters comprise the size of each of the members and the size of a gap between said members.

17. a method for diagnosing a connection life of a solder connection according to claim 12, wherein said material constants comprise the thermal expansion coefficient of each of said members.

18. A method for diagnosing a connection life of a solder connection according to claim 12, wherein said analysis condition comprises a temperature differences, and a repetition frequency.

* * * * *